United States Patent [19]

Genco et al.

[11] Patent Number: 4,618,231
[45] Date of Patent: Oct. 21, 1986

[54] ACCOMMODATIVE AMPLITUDE AND SPEED MEASURING INSTRUMENT

[75] Inventors: Louis V. Genco, Enon; Harry L. Task, Dayton, both of Ohio

[73] Assignee: The United States of America as represented by the Secretary of the Air Force, Washington, D.C.

[21] Appl. No.: 582,496

[22] Filed: Feb. 22, 1984

[51] Int. Cl.⁴ .............................................. A61B 3/02
[52] U.S. Cl. ..................................... 351/237; 351/243
[58] Field of Search ........................ 351/237, 243, 246

[56] References Cited

U.S. PATENT DOCUMENTS

| | | |
|---|---|---|
| Re. 28,921 | 8/1976 | Haines et al. |
| 3,947,099 | 3/1976 | Grolman et al. |
| 3,969,020 | 7/1976 | Lynn et al. ............................ 351/237 |
| 4,105,302 | 8/1978 | Tate ...................................... 351/237 |
| 4,155,632 | 5/1979 | Wolbarsht . |
| 4,283,126 | 8/1981 | Reiner . |
| 4,408,846 | 10/1983 | Balliet ............................. 351/237 X |
| 4,533,221 | 8/1985 | Trachtman ........................... 351/203 |

Primary Examiner—Rodney B. Bovernick
Attorney, Agent, or Firm—Bobby D. Scearce; Donald J. Singer

[57] ABSTRACT

A novel instrument and method for measuring the accommodative amplitude and speed of the eye of a subject is described. The instrument for making the measurements according to the present invention comprises a pair of illuminated or luminous visual displays disposed for viewing along an optical axis, the images of the displays superimposed upon each other for viewing by a subject, one of the displays comprising a pattern having a plurality of distinct and recognizable orientations with respect to the axis along which it is viewed, an orientation generator for randomly and alternately generating one of the orientations for viewing by the subject, a switch operable by the subject for turning the displays off and indicating the observed orientation of the random pattern, and a recorder for recording the last displayed orientation and the time the displays were on or the time between presentation of one display and the correct identification of the other.

12 Claims, 7 Drawing Figures

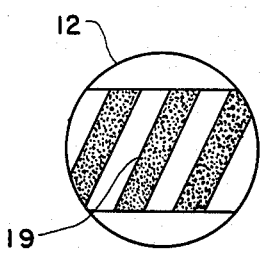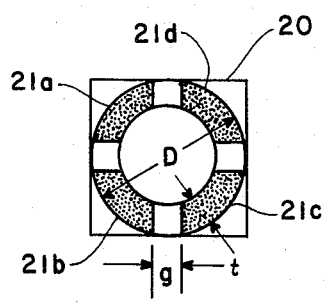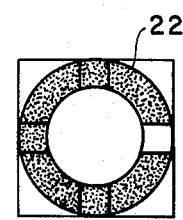
Fig. 2a  Fig. 2b  Fig. 2c
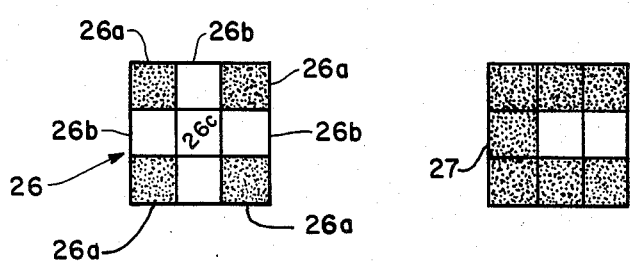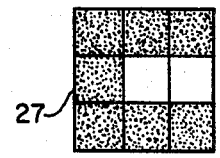
Fig. 2d  Fig. 2e

4,618,231

ACCOMMODATIVE AMPLITUDE AND SPEED MEASURING INSTRUMENT

RIGHTS OF THE GOVERNMENT

The invention described herein may be manufactured and used by or for the Government of the United States for all governmental purposes without the payment of any royalty.

BACKGROUND OF THE INVENTION

The present invention relates generally to vision testing equipment and methods, and more particularly to a novel instrument and method for the rapid and accurate determination of the accommodative amplitude and accommodative speed of the eye.

Accommodation is a clinical term referring to the ability of eyes to adapt or adjust to permit sharp retinal focusing of images of objects viewed at different distances. The maximum amount (or amplitude) of accommodation is a measure of near vision, or of how closely the eyes can see, without blurring. As the interocular muscles and the lenses age, and as the intraocular media change chemically (e.g., with age), accommodative speed and range will also change. Normally, a person will eventually require the assistance of bifocals or reading glasses to provide for the consequent impairment with age of accommodative powers of the eyes.

The present invention provides an instrument designed to rapidly and accurately measure both the amplitude and speed of accommodation of the eye, and to record the corresponding data on magnetic tape. The instrument is characterized by its simplicity and may be battery powered for portability. The instrument comprises a first visual display, preferably in the form of a diagonal square wave pattern on a flat light-emitting diode (LED) display, a lens having a focal plane coincident with the plane of the first display, a beam splitter, a movable second visual display having a selectable display configuration and whose image is reflected onto the optical axis of the lens by the beam splitter, and control means for randomly generating and positioning the second visual display configuration for measuring and recording information relating to the speed and amplitude of accommodation.

The instrument of the present invention may be useful for quantifying changes in accommodation as a result of the aging process or due to psychophysiologic factors occurring as a consequence of changing environmental factors.

It is, therefore, a principal object of the present invention to provide a novel instrument and method for measuring the speed of accommodation of the eye.

It is another object of the present invention to provide a novel instrument and method for measuring the amplitude of accommodation of the eye.

It is a further object of the invention to provide an instrument for measuring both the speed and amplitude of accommodation of the eye and which is portable and accurate.

These and other objects of the present invention will become apparent as the detailed description of certain representative embodiments thereof proceeds.

SUMMARY OF THE INVENTION

In accordance with the foregoing principles and objects of the present invention, a novel instrument and method for measuring the accommodative amplitude and speed of the eye of a subject is described. The instrument for making the measurements according to the present invention comprises a pair of illuminated or luminous visual displays disposed for viewing along an optical axis, the images of the displays superimposed upon each other for viewing by a subject, one of the displays comprising a pattern having a plurality of distinct and recognizable orientations with respect to the axis along which it is viewed, an orientation generator for randomly and alternately generating one of the orientations for viewing by the subject, a switch operable by the subject for turning the displays off and indicating the observed orientation of the random pattern, and a recorder for recording the last displayed orientation and the time the displays were on or the time between presentation of one display and the correct identification of the other.

DESCRIPTION OF THE DRAWINGS

The present invention will be more clearly understood from the following description of certain representative embodiments thereof read in conjunction with the accompanying drawings wherein:

FIG. 2a is a schematic representation of a diagonal square wave pattern on an LED display representative of that desirable for use as the first visual display.

FIG. 2b illustrates a liquid crystal display in the form of segmented annular pattern useable as the second visual display.

FIG. 2c presents the segmented annular pattern illustrated in FIG. 2b with three of the four gaps randomly filled in to generate one of the four available "C" shaped pattern orientations.

FIG. 2d presents an alternative display pattern for use as the second visual display.

FIG. 2e presents the display pattern of FIG. 2d with selected portions illuminated to display one of the four available pattern orientations.

DETAILED DESCRIPTION

Figure 1:
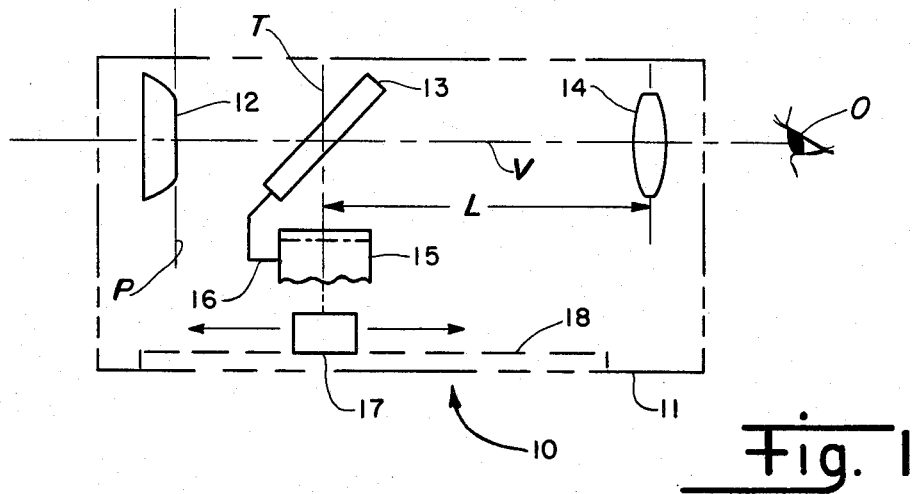
FIG. 1 is a schematic plan view of a representative configuration for the optics comprising the vision testing instrument of the present invention.

Referring now to the drawings, FIG. 1 presents a schematic plan view of a representative optical system useful in the practice of the invention, and illustrates the use of the system for the measurement of accommodative amplitude or the accommodative speed of the eye of an observer/subject O. The optical system 10 of the invention may be contained within an appropriate housing 11 to provide desirable containment and portability to the optics and associated electronics of the measuring system 10.

The optical system for the present invention may generally comprise a first visual display 12, beam splitter 13, and eyepiece lens 14 disposed along a first optical axis, or viewing axis, V, substantially as shown. Beam splitter 13 is preferably disposed substantially at a 45° angle to viewing axis V to define a second optical axis T substantially perpendicular to and intersecting optical axis V at beam splitter 13 as illustrated in FIG. 1. A second visual display 15 is disposed along optical axis T as shown such that the image thereof is reflected onto and along viewing axis V by beam splitter 13 so that both displays 12 and 15 may selectively be simultaneously or alternately observed by subject O. Beam splitter 13 and visual display 15 are interconnected structurally by conventional means 16 so as to be movable as an assembly back and forth along and parallel to viewing axis V in the direction of the arrows. Motor/controller 17 provides the means to controllably move the beam splitter 13 and display 15 assembly as suggested in FIG. 1 along a suitable supporting structure 18.

Display 12 may comprise a diagonal square wave pattern 19 on a flat light-emitting diode (LED) display as suggested in FIG. 2a. Displays 12 and 15 may, within the scope of the present invention, include luminous or illuminated displays other than LED displays, such as liquid crystal displays, self-luminous displays, and the like. Pattern 19 of display 12 provides a fixed reference display upon which subject O may fixate during measurement of accommodative speed according to procedures hereinafter described, and may be configured substantially identically to display 15 for certain accommodative speed measurements. Display 12 is disposed at the focal plane P of lens 14 so that light from display 12 reaching subject O is substantially collimated along viewing axis V.

Display 15 may comprise a flat LED which illuminates a liquid crystal display (LCD) viewed along axis T. Display 15 is configured to provide an image having a plurality of distinct and recognizable orientations with respect to the axis V along which it is viewed. For example, display 15 may have a randomly generated configuration such as illustrated schematically in FIGS. 2b and 2c or FIGS. 2d and 2e, either of which have four recognizable orientations in four mutually orthognal directions about axis V. The representative display configuration for display 15 as shown in FIG. 2b comprises essentially a Landolt letter "C" on a 5×5 square array in a segmented annular pattern 20 divided into four equal annular segments 21a,b,c,d. A space of size g between each annular segment 21 is defined to be substantially equal to the thickness t of the annular segments, and the major diameter D of the annular pattern 20 is defined to be substantially equal to five times the thickness t of the annular pattern (i.e., $D=5t$). Through the imposition of appropriate LCD control circuitry, shown schematically in FIG. 1 as incorporated into motor/controller 17, and described in more detail below in reference to FIG. 3, the spaces g between each annular segment 21 may be selectively illuminated so that a display 15 is generated which comprises an annular pattern with only one space g selectively remaining in any one of the four orientations. As shown schematically in FIG. 2c, a representative pattern may then comprise an annular "C"-shaped pattern 22 having the annular segments 21a,b,c,d of FIG. 2a connected except for the space between segments 21c,d.

Alternatively, as shown in FIGS. 2d and 2e, display 15 may comprise a 3×3 square LCD display 26 comprising nine individual square LCD elements each of which may selectively be activated. The configuration of FIG. 2d may then be used to randomly generate a square "C" shaped display in any of the four orientations by providing for the four corner elements 26a to be continuously activated, selectively activating three of the four intermediate elements 26b, and maintaining the central element 26c off. One of the four obtainable square "C" shaped configurations 27 for LCD display 26 is illustrated in FIG. 2e.

Figure 3:
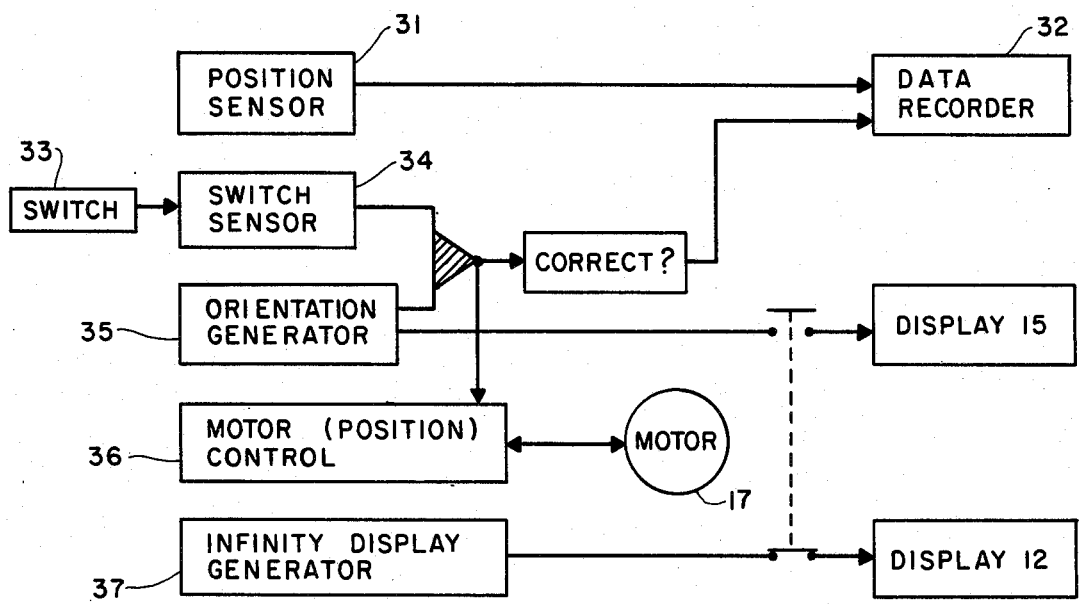
FIG. 3 is a schematic of the control and data recording electronics for the present invention.

Referring now to FIG. 3, shown therein is a schematic of the control and data recording electronics for the accommodative measuring instrument of the present invention. A position sensor 31 senses the position of the assembly 13,15 along supporting structure 18, which position is continuously recorded by data recorder 32. Paddle switch 33 has four positions corresponding to the four configurations of the pattern 22 or 27 of display 15 as suggested, respectively, in FIGS. 2b,2c or FIGS. 2d,2e. Switch 33 is operable by subject O to selectively turn display 15 off and to indicate the last observed orientation of display 15. Switch 33 is sensed in position by switch sensor 34, and signals relating to switch 33 position are fed into data recorder 32. Microcomputer controlled orientation generator 35 controls the configuration of display pattern 20 or 26 comprising display 15 to randomly provide one of the four configurations 22 or 27 for viewing by subject O. Motor control and positioning means 36 controls the positioning of the assembly 13,15 along supporting structure 18, according to a preprogrammed scheme, the measure of the accommodative amplitude being the distance between lens 14 and beam splitter 13 as hereinafter described. Infinity display generator 37 defines and controls the pattern 19 configuration of reference display 12.

In the determination of the range of accommodation of a person using the system 10 of the present invention for either accommodative speed or amplitude, the apparent image distances for each of the displays 12,15 may be determined from the expression for the focal length f of the eyepiece lens 14, $$1/f = (1/d_o) + (1/d_i)$$

it follows that, $$d_i = f d_o / (d_o - f)$$

where, $d_i$ is the apparent image distance for display 12 or 15; f is the focal length of the eyepiece lens 14; and $d_o$ is the optical distance of a display (12 or 15) from the eyepiece lens 14. The amplitude of accommodation in diopters is then equal to $1/d_i$, where $d_i$ is in meters, when display 15 is brought to the near point.

In the utilization of the optical system 10 of the present invention to measure the speed of accommodation of the eye, the speed of accommodation for eye adjustment both from distant to close objects and from close to distant objects may be determined by appropriate selection of the patterns comprising displays 12,15. The optics of the system 10 of the present invention are configured such that the fixed display 12 appears to the subject O as the distant object, and the display 15 appears as the close object. In the measurement of the accommodative speed from distant to close objects, the subject O fixates on illuminated display 12 with the beam splitter 13 and display 15 assembly positioned near display 12. Orientation generator 35 randomly selects one of the four configurations for LCD display 15, and turns display 12 off and display 15 on. Subject O observes the configuration of display 15 and trips paddle switch 33, which turns the display off, and then moves switch 33 to indicate the observed orientation of the pattern comprising display 15. The data recorder 32 records the time that display 15 was on, which is the time required by subject O to observe the orientation of the display, and compares the orientation selection of subject O to the configuration actually displayed to determine whether the response of subject O was correct. If the response was correct, assembly 13,15 is moved somewhat closer to lens 14, according to the preprogrammed scheme for motor control means 36, and the test is repeated. The foregoing test is repeated until three consecutive incorrect responses are recorded at a particular distance L (between beam splitter 13 and lens 14). The previous distance is then recorded for the corresponding maximum amplitude for the speed indicated at that distance. Accomodative speeds may be recorded at various corresponding distances. The speed of accommodation from near to distant objects may then be measured by interchanging displays 12 and 15 in the foregoing procedure.

In the measurement of accommodative amplitude, display 12 is not used. Display 15 is on constantly with the orientation generator 35 randomly selecting one of the four configurations as described above. Assembly 13,15 is moved toward subject O along viewing axis V. At a preprogrammed position the assembly 13,15 stops and display 15 stabilizes; the subject O trips switch 33 as soon as the displayed orientation is recognized, and then moves switch 33 to the position corresponding to the observed orientation. Display 15 is then turned on again and goes to random mode under control of orientation generator 35 while assembly 13,15 is moved closer to subject O. The test is repeated until three successive incorrect responses are recorded. The previous distance is then recorded as the absolute accommodative amplitude for that subject O.

The present invention, as herein described, therefore provides a novel apparatus and method for measuring the amplitude and speed of accommodation of the eye of a subject. It is understood that certain modifications to the invention may be made, as might occur to one with skill in the field of this invention, within the scope of the appended claims. Therefore, all embodiments contemplated hereunder have not been shown in complete detail. Other embodiments may be developed without departing from the spirit of the invention or from the scope of the appended claims.

We claim:

1. An instrument for measuring the accommodative speed of the eye of a subject, comprising:
   a. a first visual display in a preselected pattern, said first display disposed a predetermined distance from said subject for viewing along a first optical axis;
   b. a second visual display in a preselected pattern disposed along a second optical axis intersecting said first axis;
   c. at least one display of said first display and said second display comprising a pattern having a plurality of distinct and recognizable orientations with respect to the axis along which said at least one display is viewed;
   d. imaging means, intermediate said first display and said subject, for optically imaging said second display along said first axis and thereby superimposing the image of the pattern of said second display onto the image of the pattern of said first display for viewing by said subject along said first axis;
   e. means, structurally interconnecting said second display and said imaging means, for selective positioning of said second display, and said imaging means along a direction parallel to said first axis and between said first display and said subject;
   f. electronic means, operatively connected to said first display and said second display, for randomly and alternately generating the patterns thereof, and for randomly generating said at least one display in any one of said plurality of orientations;
   g. switching means operable by said subject and connected to said first display and said second display for selectively turning the displays on and off; and
   h. recording means, operatively connected to said switching means and said electronic means for recording the last displayed orientation and the interval of time the displays were on.

2. The instrument as recited in claim 1 wherein said imaging means comprises a beam splitter disposed at the intersection of said first axis and said second axis.

3. The instrument as recited in claim 1 wherein said electronic means alternately and randomly generates patterns of said at least one display along four mutually orthogonal directions about the axis along which said at least one display is viewed.

4. The instrument as recited in claim 1 wherein said first display and said second display include a liquid crystal display.

5. The instrument as recited in claim 1 wherein said first display and said second display include a plurality of light-emitting diodes.

6. An instrument for measuring the accommodative amplitude and speed of the eye of a subject comprising:
   a. a first visual display and second visual display each in a preselected pattern, said first display disposed a predetermined distance from said subject along a first optical axis, and said second display disposed along a second optical axis intersecting said first axis, at least one display of said first display and said second display comprising a pattern having a plurality of distinct and recognizable orientations with respect to the axis along which said at least one display is viewed;
   b. beam splitter means for optically imaging said second display along said first axis and thereby superimposing the image of said second display onto the image of said first display for viewing by said subject along said first axis;
   c. moving means, structurally interconnecting said second display and said beam splitter means, for selective positioning of said second display and said beam splitter means along a direction parallel to said first axis and between said first display and said subject;
   d. electronic means, operatively connected to said at least one display, for randomly and alternately generating the pattern of said at least one display in any one of said plurality of orientations;
   e. switching means operable by said subject and connected to said first display and said second display for selectively turning the displays on and off; and
   f. recording means, operatively connected to said switching means and said electronic means, for recording the last displayed orientation of said at least one display and the interval of time the displays were on.

7. The instrument as recited in claim 6 wherein said electronic means alternately and randomly generates the pattern of said at least one display along four mutually orthogonal directions.

8. The instrument as recited in claim 6 wherein said switching means includes means operable by said subject for indicating the last observed orientation.

9. The instrument as recited in claim 8 further comprising means for comparing said last observed orientation with said last displayed orientation, and for providing an output signal relative to the agreement of said last observed orientation by said subject with said last displayed orientation.

10. A method for measuring the accommodative speed of the eye of a subject comprising:
   a. providing a first visual display in a preselected pattern for viewing by said subject along a first optical axis;
   b. providing a second visual display in a preselected pattern disposed along a second optical axis intersecting said first axis, at least one display of said first display and said second display comprising a pattern having a plurality of distinct and recognizable orientations with respect to the axis along which said at least one display is viewed;
   c. optically imaging said second display along said first axis and superimposing the image thereof onto the image of said first display for viewing by said subject along said first axis;
   d. randomly and alternately generating the pattern of said at least one display in any one of said plurality of orientations;
   e. providing switching means operable by said subject and connected to said first display and said second display for selectively turning the displays on and off; and
   f. recording the last displayed orientation and the interval of time the displays were on.

11. The method recited in claim 10 wherein said switching means includes means operable by said subject for indicating the orientation of said at least one display last observed by said subject.

12. The method recited in claim 11 further comprising the step of comparing said last observed orientation with said last displayed orientation for determining the agreement of said orientation last observed by said subject with said last displayed orientation.

* * * * *